United States Patent

Kuwabara

[11] Patent Number: 6,023,496
[45] Date of Patent: Feb. 8, 2000

[54] X-RAY FLUORESCENCE ANALYZING APPARATUS

[75] Inventor: Shoji Kuwabara, Ibaraki, Japan

[73] Assignee: Shimadzu Corporation, Kyoto, Japan

[21] Appl. No.: 09/055,249

[22] Filed: Apr. 6, 1998

[30] Foreign Application Priority Data

Apr. 30, 1997 [JP] Japan .................. 9-126272

[51] Int. Cl.⁷ .................................................. G01N 23/00
[52] U.S. Cl. ........................................ 378/45; 378/85
[58] Field of Search .......................... 378/44, 45, 49, 378/83, 85, 84, 145

[56] References Cited

U.S. PATENT DOCUMENTS

| | | | |
|---|---|---|---|
| 3,160,749 | 12/1964 | Spielberg | 378/85 |
| 3,898,455 | 8/1975 | Furnas, Jr. | 378/85 |
| 4,134,012 | 1/1979 | Smallbone et al. | 378/47 |
| 4,599,741 | 7/1986 | Wittry | 378/85 |
| 5,132,997 | 7/1992 | Kojima et al. | 378/85 |
| 5,199,057 | 3/1993 | Tamura et al. | 378/43 |
| 5,204,887 | 4/1993 | Hayashida et al. | 378/43 |
| 5,579,363 | 11/1996 | Ingal et al. | 378/84 |

FOREIGN PATENT DOCUMENTS 1 219 448  1/1971  United Kingdom .

*Primary Examiner*—David P. Porta
*Assistant Examiner*—Drew A. Dunn
*Attorney, Agent, or Firm*—Kanesaka & Takeuchi

[57] ABSTRACT

An X-ray fluorescence analyzing apparatus is formed of an X-ray tube, plural X-ray spectroscopes disposed around a line linking between the X-ray tube and a place where a sample is placed, and first and second slit plates. The first slit plate has at least one first slit therein and is situated at an incident side of the X-ray spectroscopes. The second slit plate has at least one second slit therein, and is situated at an ejection side of the X-ray spectroscopes. X-rays radiated from the X-ray tube enter into the predetermined X-ray spectroscope through the first slit plate and then pass through the second slit plate, so that a sample is irradiated by predetermined X-ray wavelengths. The sample can be radiated by different X-ray wavelengths by selecting the slits of the first and second slit plates.

8 Claims, 3 Drawing Sheets

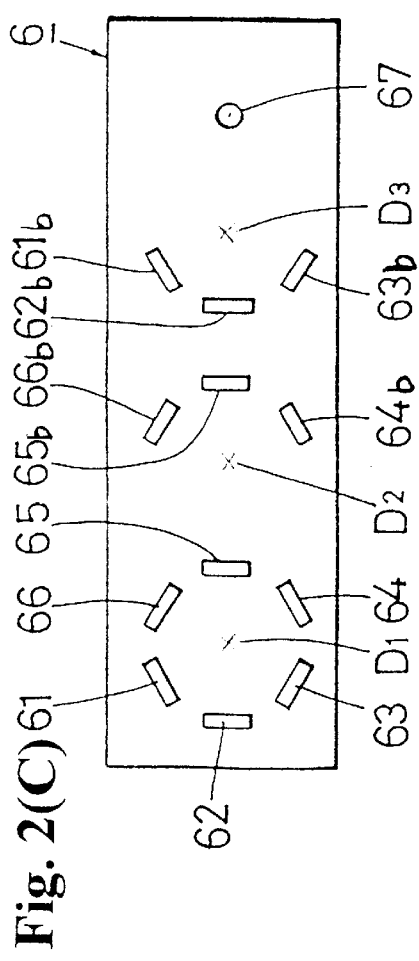
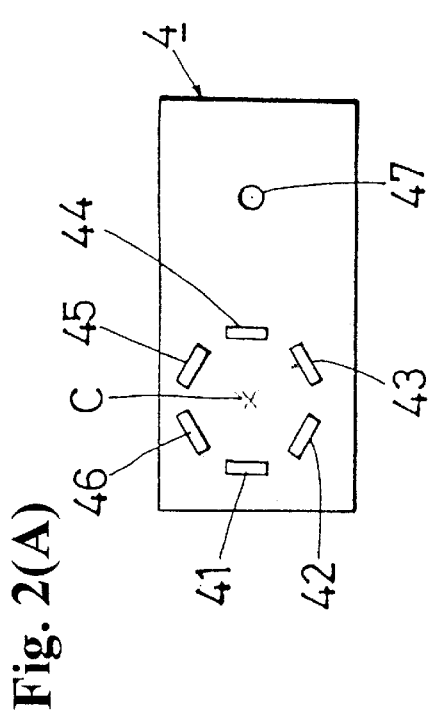

Figure 1:
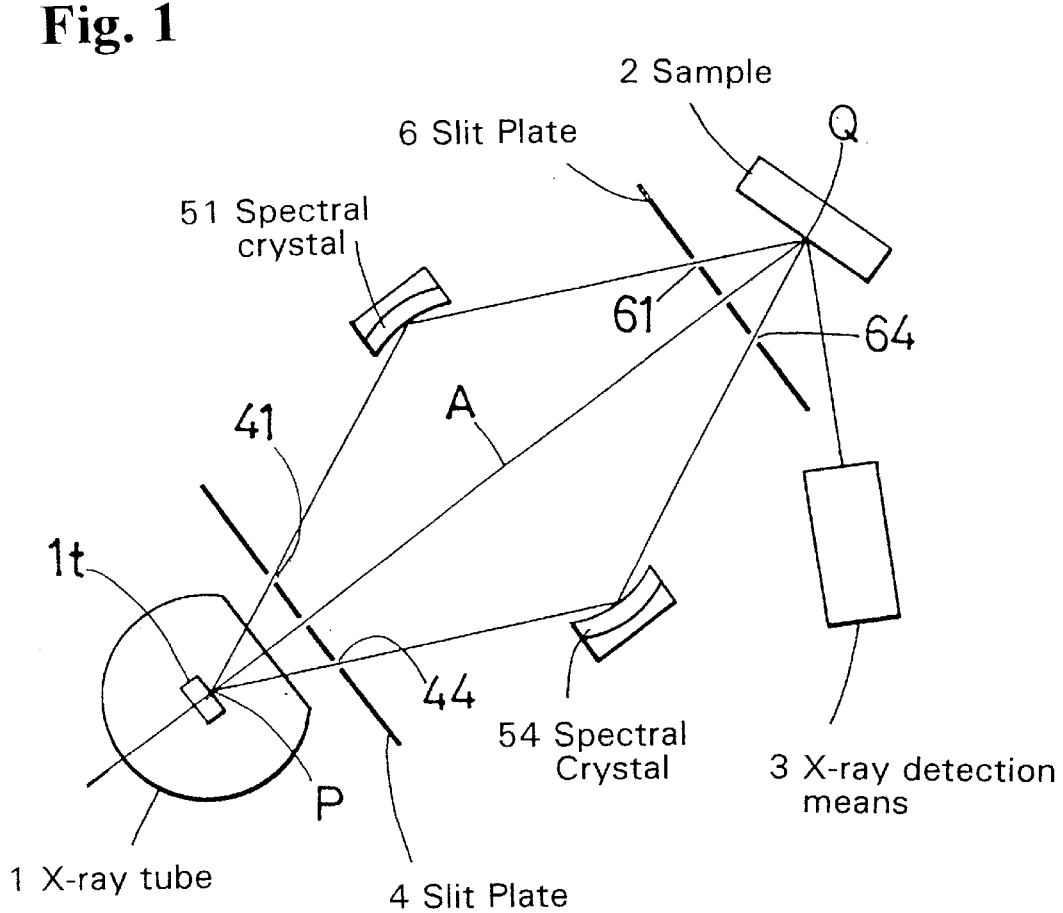

X-RAY FLUORESCENCE ANALYZING APPARATUS

BACKGROUND OF THE INVENTION AND RELATED ART STATEMENT

The present invention relates to an X-ray fluorescence analyzer or analyzing apparatus, which can use X-rays with plural kinds of wavelengths as X-rays for excitation.

In an X-ray fluorescence analyzer, in order to reduce a background, X-rays for excitation, i.e. primary X-rays, to be ejected or irradiated to a sample are processed to become monochrome by passing through an X-ray spectroscope or X-ray spectrometer. In this case, the wavelength of X-ray being processed to become monochrome is selected to a characteristic X-ray wavelength for an element to be detected in a sample or a wavelength close thereto. Therefore, in case there are several elements to be detected, and if there is only one primary X-ray spectroscope, the several elements can not be detected and metered at the same time. Thus, it takes time to analyze these elements. Accordingly, an X-ray fluorescence analyzer which can radiate at the same time primary X-rays of plural kinds of wavelengths has been used.

The conventional X-ray fluorescence analyzer which can radiate at the same time the primary X-rays of plural kinds of wavelengths is provided with an X-ray tube and an X-ray spectroscope for each wavelength. The selection or changing of the wavelength is made according to one or plural X-ray wavelengths as desired, by turning on or off of one or plural power sources of the corresponding X-ray tubes, or opening or closing one or plural shutters for the respective X-ray tubes.

The above conventional analyzer or apparatus has the following drawbacks.

Since plural X-ray tubes and X-ray spectroscopes are utilized, the apparatus becomes large and expensive.

Even if the selection or changing of the X-ray wavelengths to be used is made by turning on or off of the power source, or opening or closing the shutter, the selection or changing causes the apparatus complicated to increase the price of the apparatus. Also, it takes time to change the wavelengths.

The present invention has been made to solve the above problems of the conventional X-ray fluorescence analyzer or analyzing apparatus utilizing the primary X-rays of plural kinds of wavelengths.

SUMMARY OF THE INVENTION

An X-ray fluorescence analyzing apparatus of the invention comprises an X-ray tube, plural X-ray spectroscopes disposed around a linear line linking between an X-ray generating point and an analyzing point on a sample face, entrance or first slits situated at an incident side of the X-ray spectroscopes to allow X-rays to enter into spectral crystals of the predetermined X-ray spectroscopes, respectively, and ejection or second slits situated at an ejection side of the X-ray spectroscopes to allow the X-rays from the spectral crystals toward the sample to only pass therethrough. The X-ray spectroscope has an incident point at which the X-ray tube generates the X-rays, and a convergent point which is the analyzing point on the sample face.

BRIEF DESCRIPTION OF THE DRAWINGS

FIG. 1 is an explanatory plan view of one embodiment of the present invention;

FIGS. 2(A)–2(C) are front views of slit plates used in the embodiment shown in FIG. 1; and FIG. 3 shows X-ray spectra showing that two kinds of elements can be analyzed by primary X-rays of two kinds of wavelengths.

DETAILED DESCRIPTION OF PREFERRED EMBODIMENTS

One of the embodiments of the invention is shown in FIG. 1. In this embodiment, it is structured that three kinds of primary X-rays are taken and used. In the drawing, numeral 1 is an X-ray tube; numeral 2 is a sample; and numeral 3 is X-ray detection means, which detects fluorescent X-rays ejected or radiated from the sample.

A point P of a target it of the X-ray tube 1 is a focal point of an electron beam for excitation, and is a radiation point of the primary X-ray. A point Q is a sample analyzing position or an analyzing point for the sample 2. Six spectral crystals 51–56 are arranged around a linear line A linking between the points P and Q (four spectral crystals 52, 53, 55, 56 are not seen in the drawing).

Each spectral crystal is a curved crystal, and is located on each Rowland circle passing through the points P and Q, to thereby form an X-ray spectroscope wherein the point P is an X-ray incident point and the point Q is an X-ray convergent point. In these spectroscopes, two spectroscopes form one pair to take or obtain one X-ray wavelength. Incidentally, numeral 4 is an X-ray incident slit plate, and numeral 6 is an X-ray ejection slit plate.

FIG. 2(A) is a front view of the X-ray incident slit plate 4. The slit plate 4 is movable in a vertical direction in FIG. 1, and two groups of slit holes 41–46 and 47 are formed. The slit holes 41–46 are arranged at 60 degrees different from each other relative to a point C as a center. The distances from the center to the respective slit holes are set to values determined by the kind of the spectral crystals corresponding to the respective slit holes and the wavelength of the X-ray to be ejected. The slit plate 4 can take two positions such that the line A can pass through the point C and the center of the slit hole 47.

FIG. 2(B) is a front view of the slit plate 6. The slit plate 6 is also movable in the vertical direction in FIG. 1. In the slit plate 6, five groups of slit holes are formed. The first group is formed of slit holes 61–66 corresponding to all the spectral crystals 51–56; the second group includes slit holes 63*a*, 64*a* corresponding to the slit holes 63, 64 for the first group; the third group includes slit holes 65*a*, 66*a*; fourth group includes two slit holes 61*a*, 62*a*; and the fifth group includes only one central hole 67. The slits of the slit plate 6 for the respective groups are arranged relative to points $D_1$–$D_5$ as centers, respectively. In regard to the slit holes 61*a*–66*a* in the respective groups, the slit holes in the same numbers are located at the same distances away from the centers in the respective slit holes 61–66. The distances are set to form spectroscopes for obtaining the X-rays with the desired wavelengths by the slit holes 41–46 of the slit plate 4 and the corresponding spectral crystals 51–56.

The slit plate 4 is set such that the point C is located on the center line A, and the center of the point $D_1$ of the slit holes in the first group of the slit plate 6 is located on the center line A in FIG. 1. When the X-ray tube is turned on, X-rays with three kinds of wavelengths irradiate the point Q on the sample at the same time. Also, when the location of the slip plate 4 remains as stated above, and in case, for example, the point $D_3$ of the slit plate 6 is located on the center line A in FIG. 1, the X-ray with one wavelength selected by the spectral crystals 55, 56 is only irradiated on the sample. In case the slit hole 47 of the slit plate 4 and the slit hole 67 in the fifth group on the slit plate 6 are located on the center line A as shown in FIG. 1, it is possible to radiate the sample by the X-rays with all the wavelengths ejected from the X-ray tube 1. Therefore, there is no structural and operational complications, such as by turning on and off of plural X-ray tubes to select or change the X-rays to be irradiated.

In the present invention, a desired type of X-ray detection means may be used, such as a device to be able to scan wavelengths by using spectral crystals, a device having an ability to select wavelengths like a proportional counter tube, or a counter tube to be able to detect X-rays with all the wavelengths. In case the primary X-rays with plural kinds of wavelengths as stated in the above example is irradiated, a plurality of proportional counter tubes is designed to have windows corresponding to the X-ray wavelengths, which are desired to be detected, respectively, so that it is possible to detect and meter plural elements at the same time.

The target 1t of the X-ray tube 1 radiates continuous X-rays and, in addition, characteristic X-rays with the elements contained therein. The respective X-ray spectroscopes formed of the slit plate 4, the spectral crystals 51–56 and the slit plate 6 are set to match the wavelengths of these characteristic X-rays according to their locations and the kinds of the spectral crystals. The sample is being irradiated while the X-rays in the characteristic X-rays are selected.

For example, the target is Rh, and RhK$\alpha$-rays and RhL$\alpha$-rays are radiated; (200) phase of LiF is used for the spectral crystals 51–53 corresponding to RhK$\alpha$-rays, and TAP is used for the spectral crystals 54–56 for RhL$\alpha$-rays. In this selection, a sample is irradiated with both RhL$\alpha$-rays and RhK$\alpha$-rays. In this combination, three spectral crystals correspond to one X-ray wavelength, so that two kinds of X-ray wavelengths can be taken out or obtained. It is possible to design such that the six spectral crystals provide all different X-ray wavelengths, respectively. However, instead, it is possible to enhance the X-ray strength of one X-ray wavelength. Namely, in case two spectral crystals form one unit, X-rays with double strengths can be obtained, and in case three spectral crystals form one unit, X-rays with triple strengths can be obtained. In case the primary X-ray is made to have two wavelengths, the slit plate 6 may additionally have two groups of slit holes 64b–66b and 61b–63b, as shown in FIG. 2(C).

Figure 3:
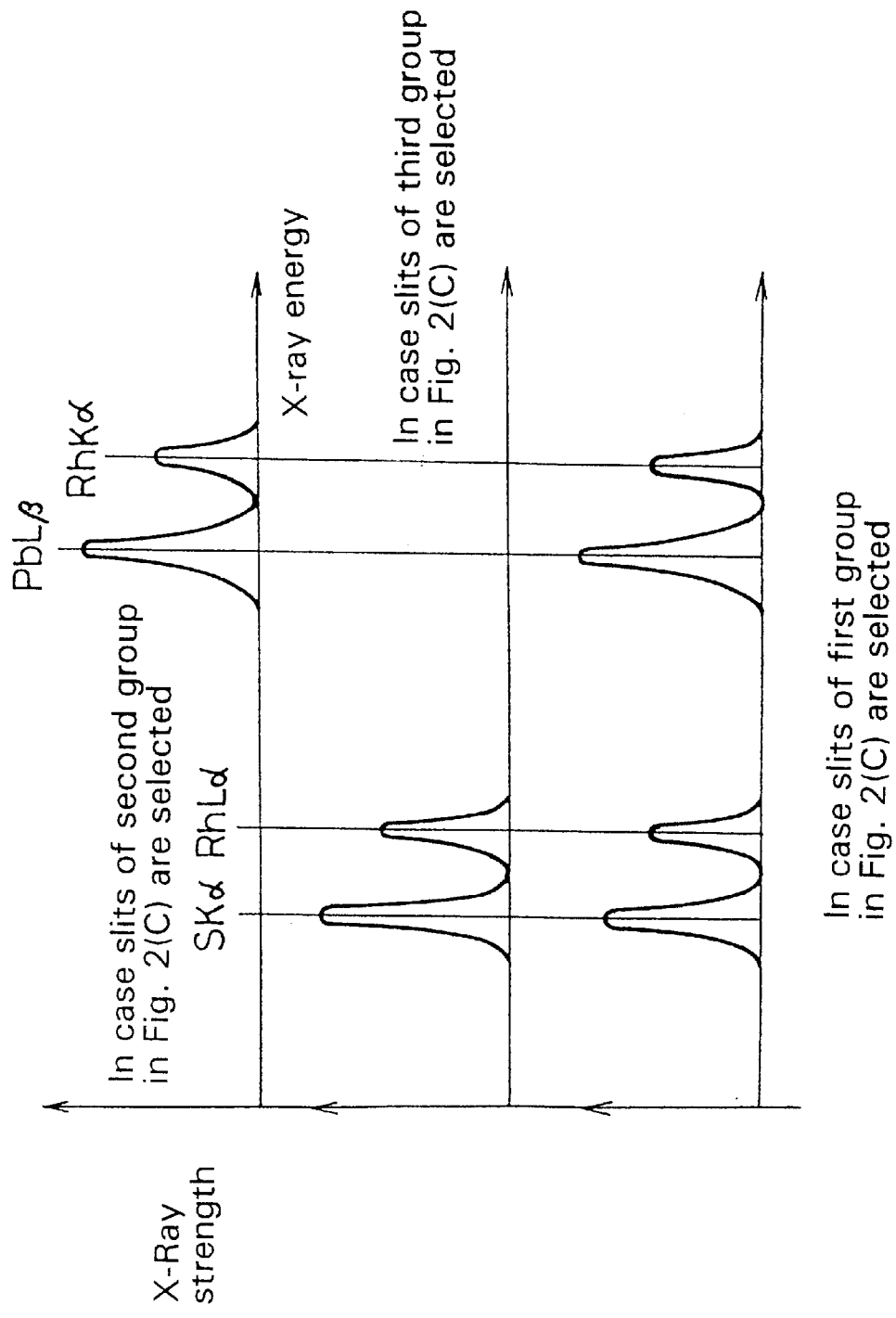

As stated above, in case the L$\alpha$-ray and K$\alpha$-ray of Rh are used, as understood from the characteristic X-ray spectra shown in FIG. 3, SK$\alpha$-ray and PbL$\beta$-ray of S, Pb and so on in the sample can be detected as fluorescent X-rays.

In the above examples, two or three kinds of the primary X-ray wavelengths are selected, but in the invention, the kinds of the primary X-ray wavelengths to be selected are not limited. Also, the number of the spectral crystals need not be six, and can be four, eight or other numbers. When the number of the spectral crystals is increased, and the responsible angular range of the respective X-ray spectroscopes around the center line A in FIG. 1 is reduced, utility effectiveness of the X-rays can be increased.

In the present invention, one or plural kinds of the primary X-ray wavelengths can be selected at the same time by one X-ray tube and irradiated to a sample. Therefore, the apparatus can be made compact as compared to an apparatus utilizing plural X-ray tubes and spectroscopes. In the invention, plural spectroscopes are utilized, but since the spectroscopes are arranged around one linear line linking between the X-ray tube and the sample, the apparatus can be made especially compact. Also, utility effectiveness of the X-rays is increased. Further, the selection of the primary X-rays is not made by turning on or off of the X-ray tube, and is made by selecting one of the groups of the slits. Thus, it is not necessary to wait for rising of the selected X-ray tube, so that plural kinds of elements can be analyzed quickly.

While the invention has been explained with reference to the specific embodiments of the invention, the explanation is illustrative and the invention is limited only by the appended claims.

What is claimed is:

1. An X-ray fluorescence analyzing apparatus comprising:
   an X-ray tube,
   plural X-ray spectroscopes disposed around a line linking between the X-ray tube and a place where a sample is placed,
   a first slit plate having at least one first slit therein, said first slit plate being situated at an incident side of the X-ray spectroscopes to allow X-rays irradiated from the X-ray tube to pass through the at least one first slit and to enter into a predetermined X-ray spectroscope, and
   a second slit plate having at least one second slit therein, said second slit plate being situated at an ejection side of the X-ray spectroscopes to allow said X-rays entering into the predetermined X-ray spectroscope to pass through the at least one second slit so that the sample is irradiated by the predetermined X-rays.

2. An X-ray fluorescence analyzing apparatus according to claim 1, wherein said X-ray spectroscopes have an incident point at which the X-ray tube generates X-rays, and a convergent point at which the sample is located.

3. An X-ray fluorescence analyzing apparatus according to claim 2, wherein each of said X-ray spectroscopes is located on a Rowland circle passing through the incident point and convergent point.

4. An X-ray fluorescence analyzing apparatus according to claim 3, wherein two of said X-ray spectroscopes form a pair to take one X-ray wavelength.

5. An X-ray fluorescence analyzing apparatus according to claim 1, wherein said first slit plate includes a plurality of groups of the first slits, one group in the first slit plate being situated at the incident side, and said second slit plate includes a plurality of groups of the second slits, one group in the second slit plate being situated at the ejection side.

6. An X-ray fluorescence analyzing apparatus according to claim 5, wherein said first and second slit plates are arranged perpendicularly to said line linking between the X-ray tube and the place where the sample is placed, and are movable perpendicularly relative to said line.

7. An X-ray fluorescence analyzing apparatus according to claim 6, wherein each of said first and second slit plates includes at least a first group of slits corresponding a number of the X-ray spectroscopes, and a second group having one slit.

8. An X-ray fluorescence analyzing apparatus according to claim 1, further comprising X-ray detection means situated near the sample for receiving X-rays passing through the sample.

* * * * *